United States Patent [19]

Coates et al.

[11] Patent Number: 4,607,008

[45] Date of Patent: * Aug. 19, 1986

[54] ENZYME/IMMUNOFLUORESCENT ASSAY FOR ANTI-EPSTEIN-BARR VIRUS ANTIBODIES

[75] Inventors: Stephen R. Coates, Lafayette; Walter L. Binder, San Diego, both of Calif.

[73] Assignee: American Hoechst Corporation, Somerville, N.J.

[*] Notice: The portion of the term of this patent subsequent to Dec. 11, 2001 has been disclaimed.

[21] Appl. No.: 586,477

[22] Filed: Mar. 5, 1984

[51] Int. Cl.$^4$ .................... G01N 33/53; C12Q 1/70; C12Q 1/28
[52] U.S. Cl. ............................. 435/7; 435/5; 435/28
[58] Field of Search ............. 436/504, 800, 519, 518; 435/5, 7, 28

[56] References Cited

U.S. PATENT DOCUMENTS

| | | | |
|---|---|---|---|
| 4,144,031 | 3/1979 | Acevedo et al. | 23/230 B |
| 4,228,127 | 10/1980 | Acevedo et al. | 422/61 |
| 4,385,126 | 5/1983 | Chen et al. | 436/518 |
| 4,487,830 | 12/1984 | Coates et al. | 435/7 |

FOREIGN PATENT DOCUMENTS 2067286 7/1981 United Kingdom .

*Primary Examiner*—Sidney Marantz
*Assistant Examiner*—Patricia DeSantis
*Attorney, Agent, or Firm*—James R. Cartiglia

[57] ABSTRACT

A method for the determination of anti-Epstein-Barr Virus antibodies in a test sample comprises contacting a substrate for the anti-Epstein-Barr Virus antibodies with sample; treating the contacted substrate with labeled antihuman Ig antibody selected from (a) a mixture comprising enzyme labeled antihuman Ig antibody and fluorescent labeled antihuman Ig antibody, (b) antihuman Ig antibodies labeled with an enzyme and a fluorescent label, (c) fluorescent labeled antihuman Ig antibody to which enzyme labeled antibody against the animal species from which the antibody used in the fluorescent labeled antibody was derived is subsequently added, and (d) enzyme labeled antihuman Ig antibody to which fluorescent labeled antibody against the animal species from which the antibody used in the enzyme labeled antibody was derived is subsequently added; determining the enzyme activity of the treated substrate; and determining the immunofluorescent patterns in substrates exhibiting enzyme activity. The method is useful for the rapid screening for anti-Epstein-Barr Virus antibodies for the diagnosis of Infectious Mononucleosis.

16 Claims, No Drawings

ENZYME/IMMUNOFLUORESCENT ASSAY FOR ANTI-EPSTEIN-BARR VIRUS ANTIBODIES

BACKGROUND OF THE INVENTION

Immunofluorescence is routinely employed in testing human serum for the presence of anti-Epstein-Barr-Virus (EBV) antibodies associated with Infectious Mononucleosis. The immunofluorescent antibody technique consists of two antigen-antibody reactions. The first reaction takes place between anti-EBV antibody contained in the serum sample and specific antigen localized in a particular substrate. The second reaction is between the anti-EBV antibody/antigen complex and antihuman immunoglobulin (Ig) antibody that has been tagged with a fluorescent label. After the second reaction, the substrate is examined for fluorescence using the fluorescent microscope. In positive samples, the patterns of fluorescence are used as indicators for the stage of Infectious Mononucleosis which the patient is in.

In spite of its accuracy and ease of use, the immunofluorescent antibody technique has one major disadvantage. It does not allow for quick screening of a number of serum samples since each sample must be individually studied under a fluorescent microscope to ascertain whether the serum is positive or negative. Since the majority of sera routinely tested are negative for anti-EBV antibody, the advantages of a method which would eliminate microscopic examination of negative sera are obvious. Such a method would be less labor intensive and therefore less expensive.

It is an object of the present invention to provide a fast and accurate method of screening a large number of serum samples for anti-EBV antibody, which, when present, can be immediately characterized as to the stage of Infectious Mononucleosis which the patient is in by fluorescent microscopy.

SUMMARY OF THE INVENTION

The present invention relates to a method for the determination of anti-EBV antibodies. More particularly, the invention relates to a single assay method that can be used to screen test samples for the presence of anti-EBV antibody and characterize the stage of Infectious Mononucleosis which the patient is in. The unique feature of the method of the present invention resides in tagging the complex of anti-EBV antibody and specific antigen with antihuman immunoglobulin which has been tagged with both an enzyme label and a fluorescent label. It is this dual labeling that enables the assay method to be used for both detection and characterization of anti-EBV antibodies.

In summary, the present invention relates to a method for the determination of anti-EBV antibody in a test sample, comprising:
providing a substrate for said anti-EBV antibody;
contacting said substrate with test sample;
treating said contacted substrate with labeled antihuman immunoglobulin (Ig) antibody, said labeled antihuman Ig antibody selected from the group consisting of:
(a) a mixture comprising enzyme labeled antihuman Ig antibody and fluorescent labeled antihuman Ig antibody;
(b) antihuman Ig antibody labeled with an enzyme and a fluorescent label;
(c) fluorescent labeled antihuman Ig antibody to which enzyme labeled antibody against the animal species from which the antibody used in the fluorescent labeled antibody was derived is subsequently added; and
(d) enzyme labeled antihuman Ig antibody to which fluorescent labeled antibody against the animal species from which the antibody used in the enzyme labeled antibody was derived is subsequently added;
analyzing the treated substrate to determine whether it has enzyme activity; and
determining the immunofluorescent pattern of a resultant enzyme active substrate.

A first preferred aspect of the present invention relates to that embodiment wherein the labeled antihuman Ig antibody is a mixture comprising enzyme labeled antihuman Ig antibody and fluorescent labeled antihuman Ig antibody.

A second preferred aspect of the present invention relates to that embodiment wherein the antihuman Ig antibody labeled with both an enzyme and a fluorescent label.

A third preferred aspect of the present invention relates to that embodiment wherein the labled antihuman Ig antibody is fluorescent labeled antihuman Ig antibody to which enzyme labeled antibody against the animal species from which the antibody used in the fluorescent labeled antibody was derived is subsequently added.

DETAILED DESCRIPTION

Antibodies determined by the method of the present invention are useful as an aid to the diagnosis of Infectious Mononucleosis and to characterize the stage of the disease which the patient is in.

The detection and quantitation of anti-EBV antibodies according to the present invention is accomplished by contacting a suitable antigen substrate with test specimen; treating the contacted substrate with labeled antihuman immunoglobulin (Ig) antibody, said labeled antibody selected from the group consisting of (a) a mixture comprising enzyme labeled antibody, fluorescent labeled antibody, (b) antihuman Ig antibody labeled with an enzyme and a fluorescent label, and (c) fluorescent labeled antihuman Ig antibody to which enzyme labeled antibody against the animal species from which the antibody used in the fluorescent labeled antibody was derived is subsequently added, and (d) enzyme labeled antihuman Ig antibody to which fluorescent labeled antibody against the animal species from which the enzyme labeled antibody was derived is subsequently added; determining the enzyme activity of the treated substrate; and determining the immunofluorescent pattern of substrates exhibiting enzyme activity.

Substrates suitable for use in the present invention include cell cultures infected with EBV. The substrate contains the antigen used to determine the presence of anti-EBV antibody in the test specimen. For best results, it is advisable that the cell culture or other substrate material containing the antigen be prepared in such a way as to preserve antigenic determinants. This means that fixatives are best avoided, or used only with caution.

Substrates utilized herein are preferably supported on flat, transparent surfaces to facilitate the determination of immunofluorescent patterns. Particularly suitable support surfaces are afforded by tissue culture treated microtiter plates. Such plates preferably have a well bottom thickness of less than 0.5 mm which allows one to use high magnification objectives in examining the substrate. Labeled antihuman Ig antibody, used to tag the complex of antibody and substrate antigen, is selected from one of the following categories:

(a) a mixture comprising enzyme labeled antihuman Ig antibody and fluorescent labeled antihuman Ig antibody;

(b) antihuman Ig antibody labeled with an enzyme and a fluorescent label;

(c) fluorescent labeled antihuman Ig antibody to which enzyme labeled antibody against the animal species from which the antibody used in the fluorescent labeled antibody was derived is subsequently added; and (d) enzyme labeled antihuman Ig antibody to which fluorescent labeled antibody against the animal species from which the antibody used in the enzyme labeled antibody was derived is subsequently added.

Fluorochrome conjugated antisera, utilized as enzyme labeled antihuman Ig antibody herein, are available commercially or may be readily prepared by methods well known in the art. Enzymes that are particularly preferred as labeling agents include, for example, horeseradish peroxidase, alkaline phosphatase, glucose oxidase, lactoperoxidase and β-galactosidase.

In an alternative mode, antihuman Ig antibody labeled with both an enzyme and a fluorescent label is used in lieu of a mixture comprising enzyme labeled antihuman Ig antibody and fluorescent labeled antihuman Ig antibody. Fluorochrome/enzyme conjugated antisera are readily prepared by reacting a commercially available enzyme/fluorochrome conjugate with a suitably purified immunoglobulin fraction.

In another alternative mode, fluorescent labeled antihuman Ig antibody is employed. After washing the plate, enzyme labeled antibody against the animal species from which the antibody used in the fluorescent labeled antibody was derived is then added and allowed to combine with any attached fluorescent labeled antihuman Ig antibody. The labeled antibodies are available commercially or may be readily prepared by methods well known in the art. Particularly preferred are enzyme labeled goat anti-rabbit IgG after fluorescein-labeled rabbit anti-human Ig.

In another alternative mode, enzyme labeled antihuman Ig antibody is employed. After washing the plate, fluorescent labeled antibody against the animal species from which the antibody used in the enzyme labeled antibody was derived is then added and allowed to combine with any attached fluorescent labeled antihuman Ig antibody. The labeled antibodies are available commercially or may be readily prepared by methods well known in the art. Particularly preferred are fluorescein-labeled goat anti-rabbit IgG after enzyme labeled rabbit anti-human Ig.

In practicing the method of the present invention, the antigen substrate, the test sample suspected of containing anti-EBV antibody and the labeled antihuman Ig antibody are combined and handled as discussed below.

Antigen substrate for the anti-EBV antibody is contacted at room temperature with test sample suspected of containing the anti-EBV antibody. The period of contact is from 30 minutes to one hour. If the test sample contains anti-EBV antibody specific for the antigen localized in the substrate, a substrate bound anti-EBV antibody/antigen complex if formed. After repeated washings, the contacted substrate is treated with labeled antihuman Ig antibody selected from the group consisting of (a) a mixture comprising enzyme labeled antihuman Ig antibody and fluorescent labeled antihuman Ig antibody, (b) antihuman Ig antibody labeled with an enzyme and a fluorescent label, (c) fluorescent labeled antihuman Ig antibody to which enzyme labeled antibody against the animal species from which the antibody used in the fluorescent labeled antibody was derived is subsequently added, and (d) enzyme labeled antihuman Ig antibody to which fluorescent labeled antibody against the animal species from which the antibody used in the enzyme labeled antibody was derived is subsequently added. Treatment of the substrate with labeled antibody is carried out at room temperature a period of 30 minutes to one hour. If the treated substrate contains bound anti-EBV antibody, a labeled substrate is formed at this stage. After repeated washings, the enzyme activity of the substrate is determined by the addition of a specific substrate for the enzyme. A variety of substrates suitable for enzymes recited and employed herein can be found in Bergmeyer, *Methods of Enzymatic Analysis*, Academic Press, New York, 1965.

The presence of enzyme activity in the substrate can be determined visually and spectrophotometrically. In the first instance, the substrate is simply examined visually for color produced by the enzymatic cleavage of the enzyme substrate (chromogen). In the second instance, the optical density of the chromogen solution is determined and correlated with anti-EBV antibody titer which is an estimation of the amount of anti-EBV antibody in the test sample. Thus, the use of an enzyme label in the method of the present invention allows the method to be employed as either a qualitative or quantitative test for the determination of anti-EBV antibody.

Test samples which exhibit enzymatic activity are further characterized by direct examination using a fluorescent microscope with an epi illumination system to determine the immunofluorescent pattern by inverting the microtiter plate and viewing it through the bottom.

The stage of Infectious Mononucleosis which the patient is in is determined by observing the specific immunofluorescent pattern.

This is achieved by studying the specific location of fluorescence observed in the cell. If the fluorescence is localized in one discrete section of the nucleus, the Infectious Mononucleosis is at an early stage. Similarly, if the fluorescence is scattered throughout the cell cytoplasm and nucleus, the Infectious Mononucleosis is at a later stage than if the fluorescence is localized in discrete sections of the nucleus.

What is claimed is:

1. A method for the determination of anti-Epstein-Barr Virus antibody in a test sample, comprising:

providing a substrate for the anti-Epstein-Barr Virus antibody; contacting with a test sample;

treating said contacted substrate with labeled antihuman immunoglobulin antibody, said labeled antihuman immunoglobulin antibody selected from the group consisting of:

(a) a mixture comprising enzyme labeled antihuman immunoglobulin antibody and fluorescent labeled antihuman immunoglobulin antibody;

(b) antihuman immunoglobulin antibody labeled with an enzyme and a fluorescent label;

(c) fluorescent labeled antihuman immunoglobulin antibody to which enzyme labeled antibody against the animal species from which the antibody used in the fluorescent labeled antibody was derived is subsequently added; and (d) enzyme labeled antihuman immunoglobulin antibody to which fluorescent labeled antibody against the animal species from which the antibody used in the enzyme labeled antibody was derived is subsequently added;

analyzing the treated substrate to determine whether it has enzyme activity; and determining the immunofluorescent pattern in a substrate exhibiting enzyme activity.

2. The method according to claim 1 wherein said labeled antihuman antibody comprises (a).

3. The method according to claim 1 wherein said labeled antihuman antibody comprises (b).

4. The method according to claim 1 wherein said labeled antihuman antibody comprises (c).

5. The method according to claim 1 wherein said labeled antihuman antibody comprises (d).

6. The method according to claim 2 wherein said enzyme is horseradish peroxidase.

7. The method according to claim 3 wherein said enzyme is horseradish peroxidase.

8. The method according to claim 4 wherein said enzyme is horseradish peroxidase.

9. The method according to claim 2 wherein said fluorescent label is fluorescein.

10. The method acording to claim 3 wherein said fluorescent label is fluorescein.

11. The method according to claim 4 wherein said fluorescent label is fluorescein.

12. The method according to claim 2 wherein said enzyme is horseradish peroxidase and said fluorescent label is fluorescein.

13. The method according to claim 3 wherein said enyzme is horseradish peroxidase and said fluorescent label is fluorescein.

14. The method according to claim 4 wherein said enzyme is horseradish peroxidase and said fluorescent label is fluorescein.

15. The method according to claim 1 wherein said antihuman antibody is antihuman IgG.

16. The method according to claim 1 wherein said substrate comprises cell cultures infected with Epstein-Barr Virus.

* * * * *